United States Patent
Hosoi et al.

(10) Patent No.: US 7,883,211 B2
(45) Date of Patent: Feb. 8, 2011

(54) VISION TESTING SYSTEM

(75) Inventors: Yoshinobu Hosoi, Gamagori (JP); Yuichiro Kanazawa, Okazaki (JP); Hirohisa Terabe, Toyokawa (JP); Yoshihiro Ozaki, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 12/225,178

(22) PCT Filed: Apr. 25, 2007

(86) PCT No.: PCT/JP2007/058944
§ 371 (c)(1),
(2), (4) Date: Sep. 16, 2008

(87) PCT Pub. No.: WO2007/125955
PCT Pub. Date: Nov. 8, 2007

(65) Prior Publication Data
US 2009/0290122 A1 Nov. 26, 2009

(30) Foreign Application Priority Data
Apr. 28, 2006 (JP) .............................. 2006-126529

(51) Int. Cl.
*A61B 3/02* (2006.01)
*A61B 3/14* (2006.01)
*A61B 3/00* (2006.01)
(52) U.S. Cl. .................... 351/222; 351/210; 351/246
(58) Field of Classification Search ......... 351/210–212, 351/216–217, 221–222, 237, 245–246
See application file for complete search history.

(56) References Cited

U.S. PATENT DOCUMENTS

| 5,331,358 A | 7/1994 | Schurle et al. |
| 5,483,305 A | 1/1996 | Kohayakawa |
| 6,048,064 A | 4/2000 | Hosoi et al. |
| 2006/0050238 A1 | 3/2006 | Nakamura et al. |
| 2006/0139573 A1* | 6/2006 | Sakurada ................ 351/211 |
| 2006/0164599 A1* | 7/2006 | Ikezawa ................. 351/239 |

FOREIGN PATENT DOCUMENTS

| DE | 44 25 443 C1 | 2/1996 |
| EP | 1 442 697 A1 | 8/2004 |
| JP | A-64-20824 | 1/1989 |
| JP | A 5-130975 | 5/1993 |
| JP | U-5-88501 | 12/1993 |
| JP | A 9-10175 | 1/1997 |
| JP | A 11-155813 | 6/1999 |

\* cited by examiner

*Primary Examiner*—Scott J Sugarman
*Assistant Examiner*—Dawayne A Pinkney
(74) *Attorney, Agent, or Firm*—Oliff & Berridge, PLC (57) ABSTRACT

A subjective vision testing system is used for visual function tests for examinees. The subjective vision testing system is provided with an optometric apparatus which selectively sets optical elements in front of both eyes of an examinee, an optotype presenting apparatus for displaying optotypes to the examinee, and a controller. The optotype presenting apparatus, based on a command signal for implementation of a binocular balance test, displays optotypes used for binocular balance tests. The optometric apparatus, based on a command signal for implementation of a binocular balance test, sets a first prism in front of the examinee's right eye and a second prism in front of the examinee's left eye. The second prism has a base direction vertically opposite to the first prism and the same prism power as the first prism.

2 Claims, 8 Drawing Sheets

VISION TESTING SYSTEM

CROSS-REFERENCE TO RELATED APPLICATIONS

This is a national phase application based on the PCT International Patent Application No. PCT/JP2007/058944 filed on Apr. 25, 2007, the entire contents of which are incorporated herein by reference.

TECHNICAL FIELD

The present invention relates to a subjective vision testing system for testing visual functions of examinee's eyes.

BACKGROUND ART

As an optotype presenting apparatus of a vision testing system, an apparatus arranged to present an optotype or chart on a color liquid crystal display (LCD) has recently been proposed as well as a conventional apparatus arranged to present an optotype on a screen by projection. Furthermore, an apparatus with the LCD for a binocular balance test has been proposed in which two LCDs placed one before the other and two polarization filters having polarization axes perpendicular to each other. In this apparatus, as with the conventional screen projection type apparatus, two polarization filters whose polarization axes are perpendicular to each other are disposed in front of both eyes of an examinee to present an optotype for right eye and an optotype for left eye to both eyes of the examinee (see U.S. Pat. No. 5,331,358 (JP5-130975 (1993)).

However, such configuration having two LCDs and two polarization filters is complicated and expensive and leads to an increase in apparatus size.

DISCLOSURE OF INVENTION

Problems to be Solved by the Invention

The present invention has a purpose to provide a vision testing system capable of accurately performing a binocular balance test by a simple configuration.

Means for Solving the Problems

To achieve the above purpose, the invention is characterized in the following configurations.

The invention provides a subjective vision testing system for testing visual functions of eyes of an examinee, comprising: an optometric apparatus arranged to selectively dispose optical elements in front of both eyes of the examinee; a optotype presenting apparatus having a presenting part for presenting an optotype to the examinee; and a controller, wherein the optotype presenting apparatus is adapted to present an optotype for a binocular balance test based on a command signal to execute the binocular balance test from the controller, and the optometric apparatus is adapted to dispose, based on the command signal to execute the binocular balance test, a first prism in front of a right eye of the examinee and a second prism in front of a left eye of the examinee, the second prism having a base direction vertically opposite to that of the first prism and the same prism power as the first prism.

In the subjective vision testing system of the invention, preferably, the optotype for a binocular balance test includes figures for fusion stimulus which are arranged in pair one above the other and the same in shape, size, and color.

In the subjective vision testing system of the invention, preferably, each of the first and second prisms is a rotary prism.

In the subjective vision testing system of the invention, preferably, prism powers of the first prism and the second prism are changed equally.

According to the subjective vision testing system of the invention, a binocular balance test can be performed accurately by a simple configuration.

BEST MODE FOR CARRYING OUT THE INVENTION

Figure 1:
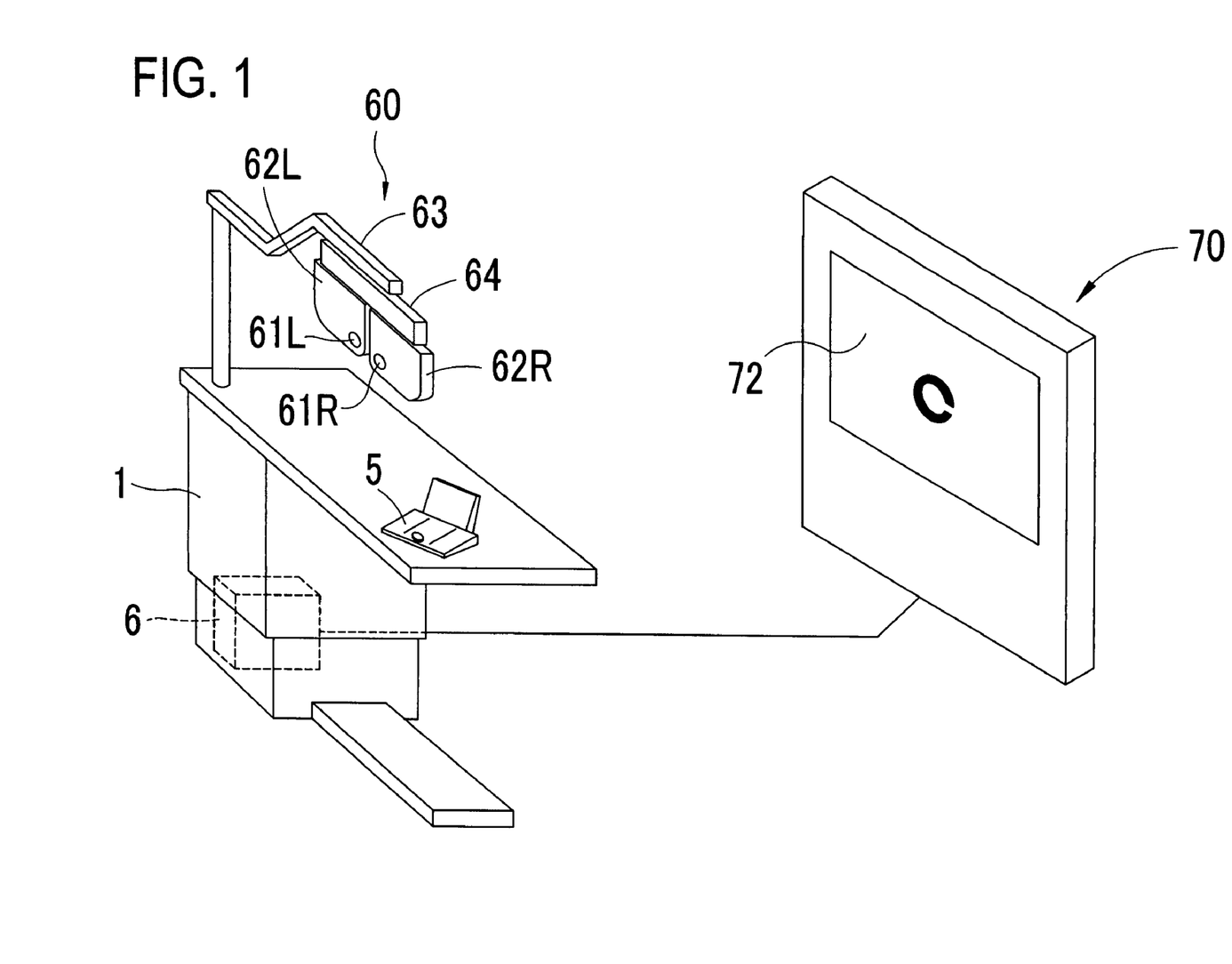
FIG. 1 is a schematic external view of a subjective vision testing system of an embodiment of the invention.

A detailed description of a preferred embodiment of the present invention will now be given referring to the accompanying drawings. FIG. 1 is a schematic external view of a subjective vision testing system of the embodiment of the present invention.

Above a table 1, an optometric apparatus 60, called a phoropter or a refractor, for subjectively testing visual functions of examinee's eyes is placed with an arm 63. The optometric apparatus 60 includes a pair of symmetric lens chamber units 62R and 62L, and a moving unit 64. The lens chamber unit 62R has a test window 61R and the lens chamber unit 62L has a test window 61L. In each inside of the lens chamber units 62R and 62L, lens disks 11 to 16 mentioned later and others are arranged. The lens chamber units 62R and 62L can be slid on the same line by the moving unit 64 provided thereon to change a distance therebetween. Furthermore, they are converged to change a convergence angle therebetween.

An optotype presenting apparatus 70 has a presenting part 72 constituted of a color liquid crystal display. An optotype or chart to be centrally displayed on the presenting part 72 is changed by operation of a controller 5 via a relay unit 6. The optotype presenting apparatus 70 is held in a position approximately level with the optometric apparatus 60 by wall-hanging, a stand, or other means.

Figure 2:
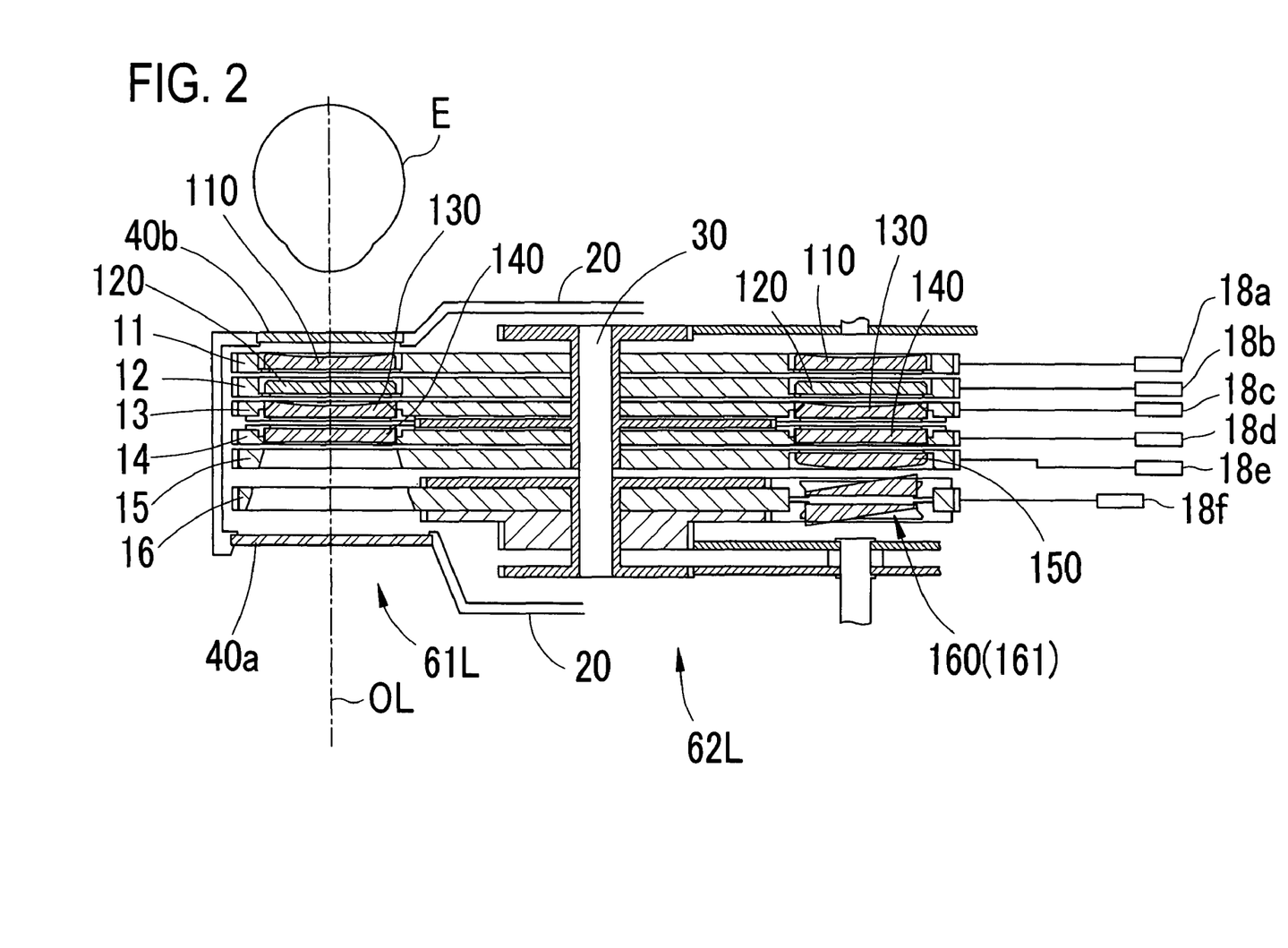
FIG. 2 is a partly sectional view showing a schematic configuration of an inside of a lens chamber unit.

FIG. 2 is a partly sectional view of the lens chamber unit 62L for left eye, viewed from above, showing rotation systems of the lens disks 11 to 16 and others. On a side of the test window 61L facing an examiner, a protective glass 40a is mounted. On the other side facing an examinee (an examinee's eye E), a protective glass 40b is mounted. In a cover 20 of the lens chamber unit 62L, six lens disks 11 to 16 on each of which an opening and a plurality of optical elements are arranged are placed to be rotatable about a shaft 30. In the lens disk 11, a plurality of spherical lenses 110 having different high powers (−18 D to +15 D (0 D is an opening) in steps of 3 D (diopter) in this embodiment) are mounted. In the lens disk 12, a plurality of spherical lenses 120 having different low powers (−1 D to +1.75 D (0 D is an opening) in steps of 0.25 D in this embodiment) are mounted. In the lens disk 13, a plurality of cylinder lenses 130 having different high powers (−7.5 D to 0 D (0 D is an opening) in steps of 1.5 D in this embodiment) are mounted. In the lens disk 14, a plurality of cylinder lenses 140 having different low powers (−1.25 D to 0 D (0 D is an opening) in steps of 0.25 D in this embodiment) are mounted. In the lens disk 15, a plurality of various first auxiliary lenses 150 are mounted. In the lens disk 16, a plurality of various second auxiliary lenses 160 are mounted. Each outer periphery of the lens disks 11 to 16 is formed with a gear. The lens disk 11 is rotated by a motor 18a, the lens disk 12 is rotated by a motor 18b, the lens disk 13 is rotated by a motor 18c, the lens disk 14 is rotated by a motor 18d, the lens disk 15 is rotated by a motor 18e, and the lens disk 16 is rotated by a motor 18f, each being rotated about the shaft 30, thereby changing optical elements to be disposed on a test optical axis OL passing the center of the test window 61L.

The first auxiliary lenses 150 of this embodiment include, besides an opening, a green filter (the lens chamber unit 62L), a red filter (the lens chamber unit 62R), a 10Δ (Prism diopter) BI (Base In) dispersion prism (the lens chamber unit 62L), a 6Δ BU (Base Up) dispersion prism (the lens chamber unit 62R), a shielding plate, and others.

The second auxiliary lenses 160 of this embodiment include, besides an opening, a rotary prism 161 and others. The rotary prism 161 consists of a combination of two (a pair of) prisms that have vertically-opposite base directions and the same prism power. The two prisms are caused to rotate in opposite directions to change prism power sequentially.

Figure 3:
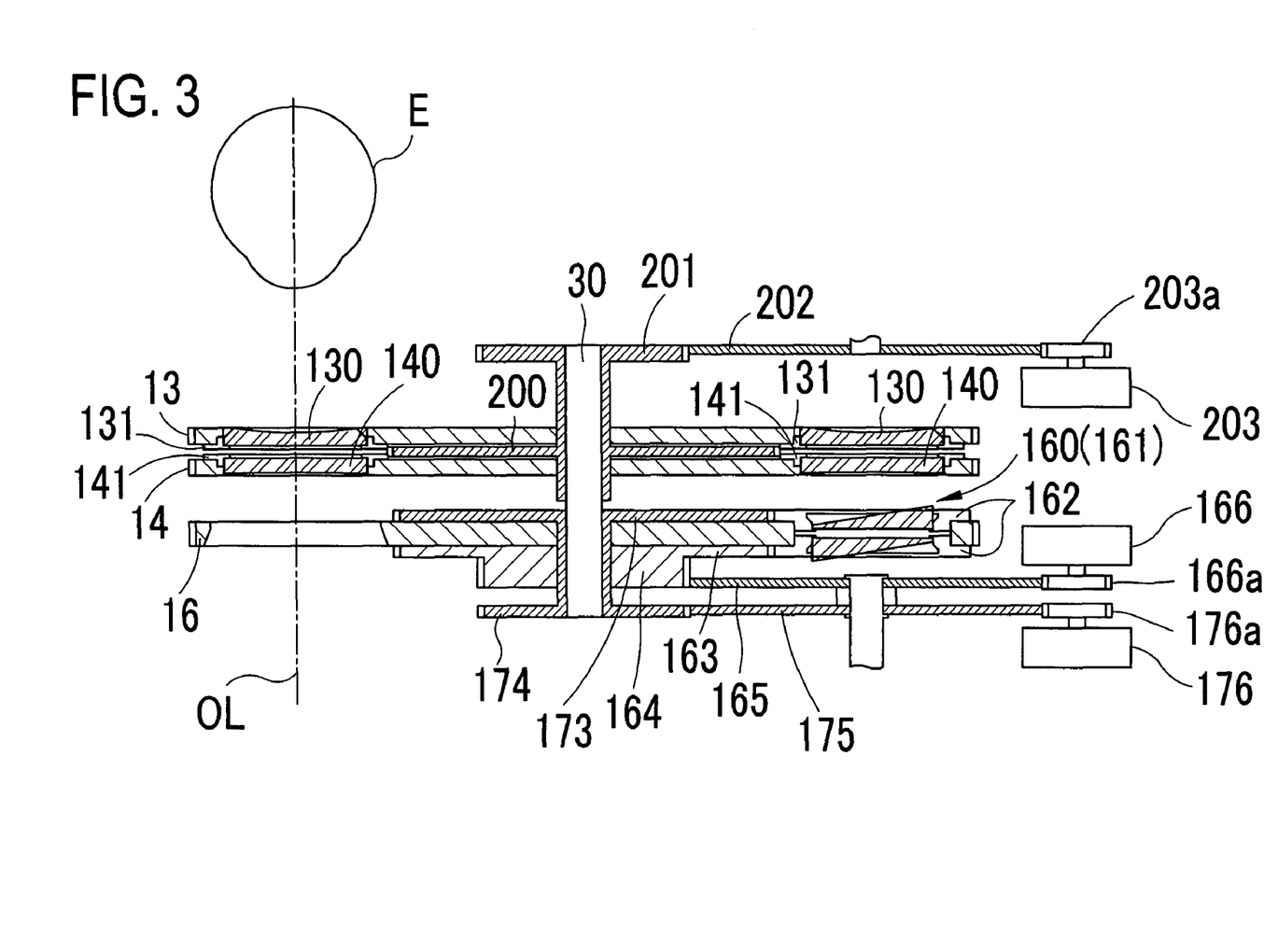
FIG. 3 is a partly sectional view showing a schematic configuration of the inside of the lens chamber unit.

FIG. 3 is a partly sectional view of the lens chamber unit 62L viewed from above, showing a rotation system for the cylinder lenses 130 and 140 and the secondary auxiliary lenses 160, and others. The cylinder lens 130 is mounted to be rotatable about the optical axis OL in the disk 13 through a holder 131 having an outer edge formed with a gear. The cylinder lens 140 is mounted to be rotatable about the optical axis OL in the disk 14 through a holder 141 having an outer edge formed with a gear. Respective gears of the holders 131 and 141 mesh with a sun gear 200 rotatable about the shaft 30. A gear 201 joined to the sun gear 200 meshes with a gear 203a attached to a rotation shaft of a motor 203 via a gear 202. Thus, the cylinder lenses 130 and 140 are rotated about the optical axis OL by the motor 203.

One of the rotary prism 161 is mounted to be rotatable about the optical axis OL in the disk 16 through one of holders 162 having an outer edge formed with a gear. The gear of the one holder 162 meshes with a sun gear 163 rotatable about the shaft 30. A gear 164 integrally formed with the sun gear 163 meshes with a gear 166a attached to a rotation shaft of a motor 166 via a gear 165. The other one of the rotary prism 161 is mounted to be rotatable about the optical axis OL in the disk 16 through the other holder 162 having an outer edge formed with a gear. The gear of the other holder 162 meshes with a sun gear 173 rotatable about the shaft 30. A gear 174 joined to the sun gear 173 meshes with a gear 176a attached to a rotation shaft of a motor 176 via a gear 175. Accordingly, the two prisms of the rotary prism 161 are rotated about the optical axis OL in opposite directions by the motors 166 and 176.

The lens chamber unit 62R is configured to be symmetric to the lens chamber unit 62L and its details are omitted.

Figure 4:
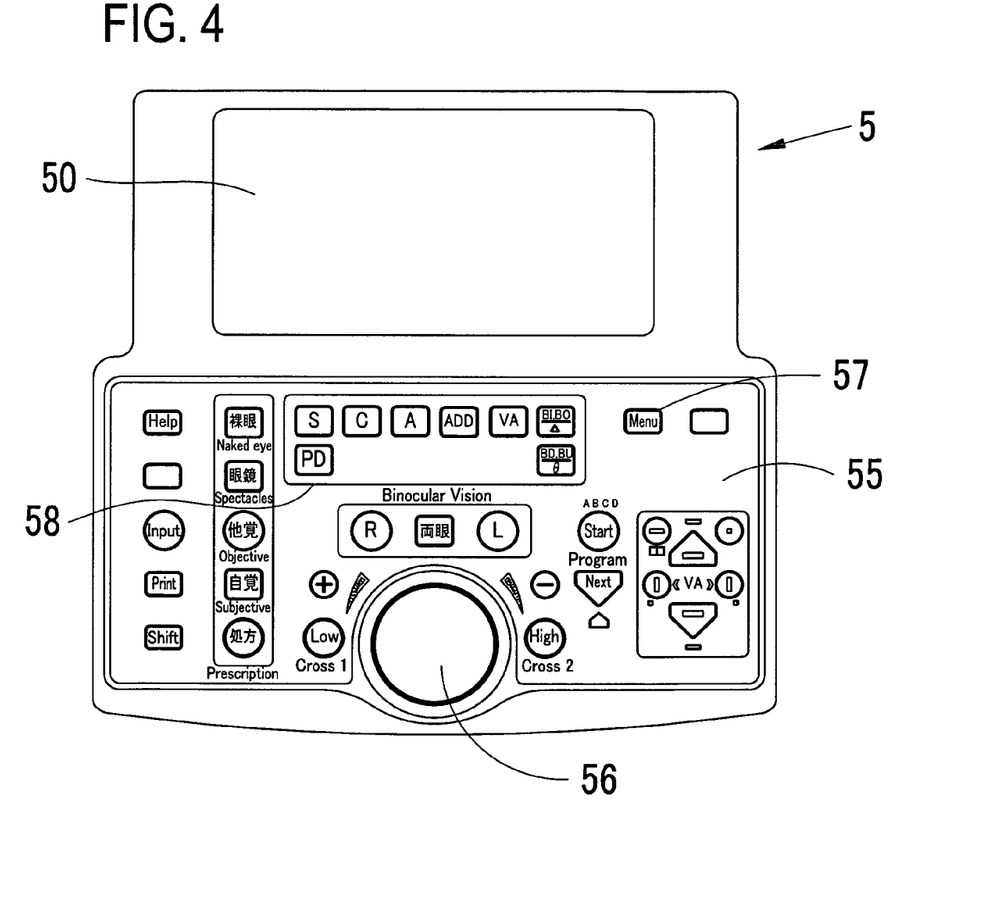
FIG. 4 is a schematic external view of a controller.

FIG. 4 is a schematic external view of the controller 5. The controller 5 has a display part 50 of a touch screen type consisting of a color liquid display and an operation part (a switch panel) 55. The operation part 55 includes operation buttons such as a dial 56, a menu button 57, and a mode button 58.

Figure 5:
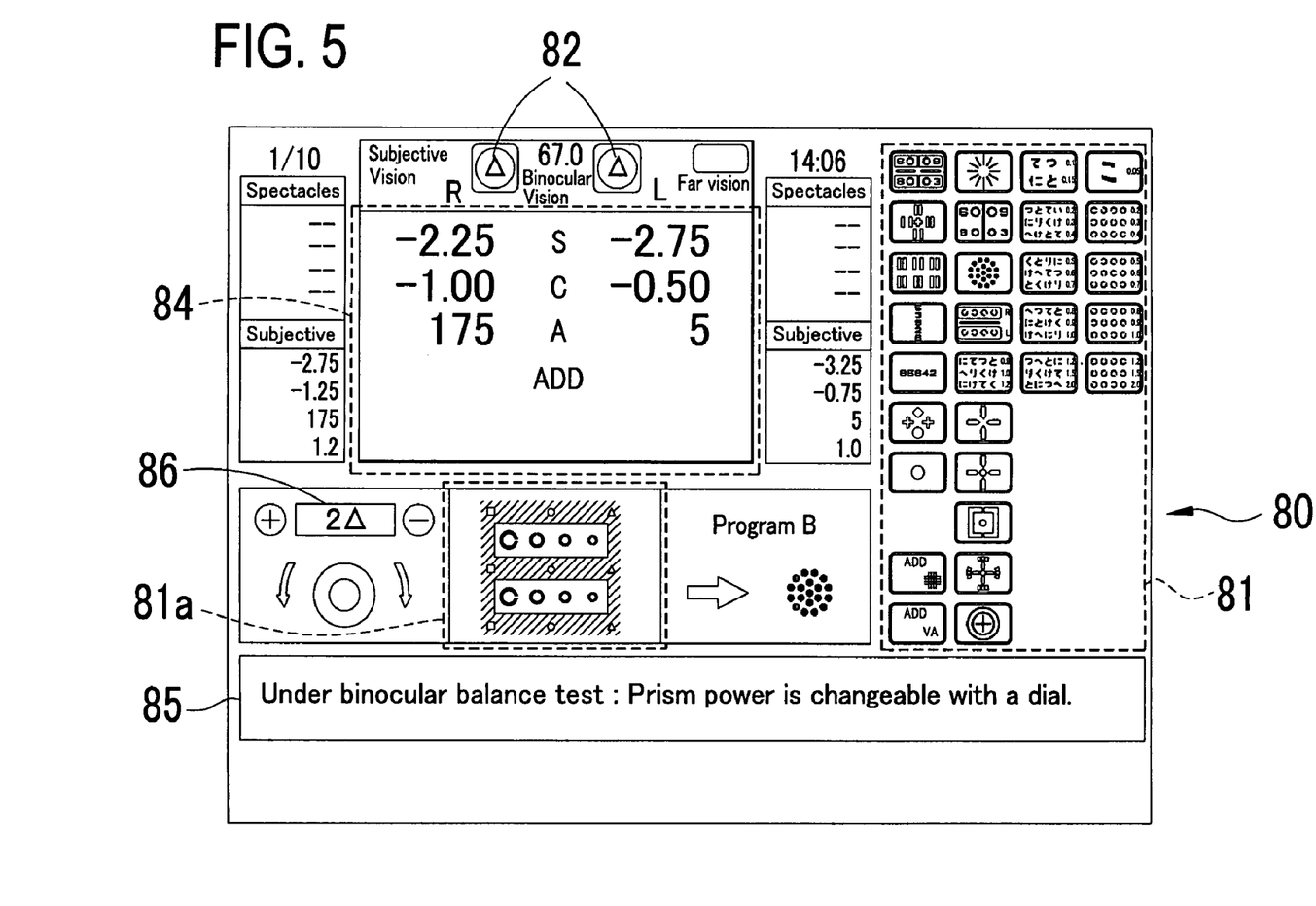
FIG. 5 is a diagram showing an example of a screen to be displayed on a display part of the controller.

FIG. 5 is a diagram showing an example of a screen to be displayed on the display part 50 during a test. This is an example of a screen 80 in the case of performing a binocular balance test after full correction powers are obtained for both eyes of the examinee. In the screen 80, there appear buttons 81 for changing (selecting) an optotype to be presented on the presenting part 72, a section 81a for indicating the optotype presented on the presenting part 72, buttons 82 for changing (selecting) the auxiliary lenses to be disposed in the test windows 61R and 61L, a section 84 for indicating power and others of the optical elements disposed in the test windows 61R and 61L, a section 85 for indicating a message, a section 86 for indicating prism power of the rotary prism 161, and others.

Figure 6:
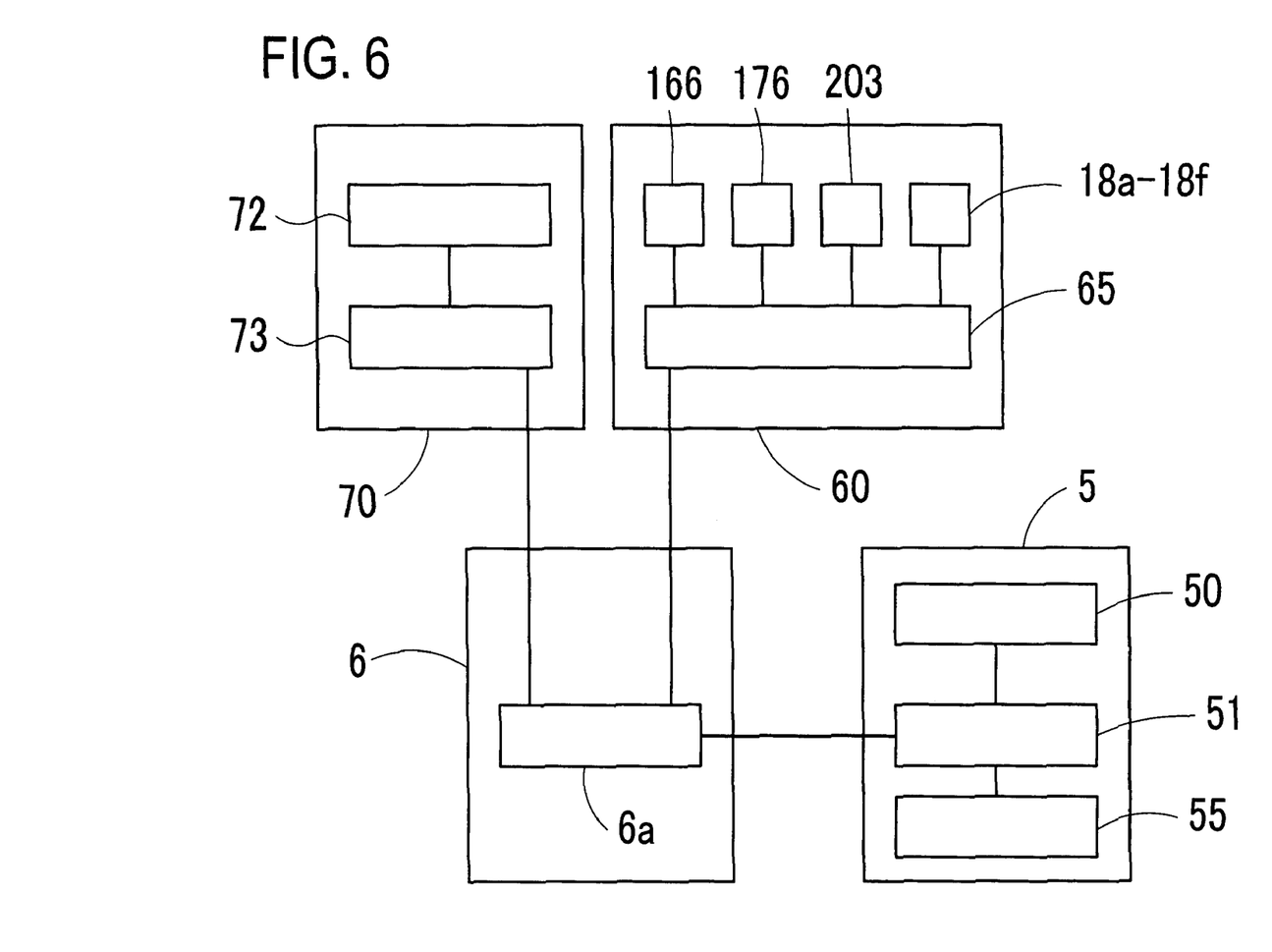
FIG. 6 is a schematic block diagram of a control system of the vision testing system.

FIG. 6 is a schematic block diagram of a control system of the vision testing system. An arithmetic control part 6a of the relay unit 6 is connected to an arithmetic control part 65 of the optometric apparatus 60, an arithmetic control part 73 of the optotype presenting apparatus 70, and an arithmetic control part 51 of the controller 5.

The binocular balance test using the rotary prism 161 in the vision testing system having the above structure will be explained. After the full correction powers are obtained for both eyes of the examinee, the binocular balance test is performed.

Figure 7A:
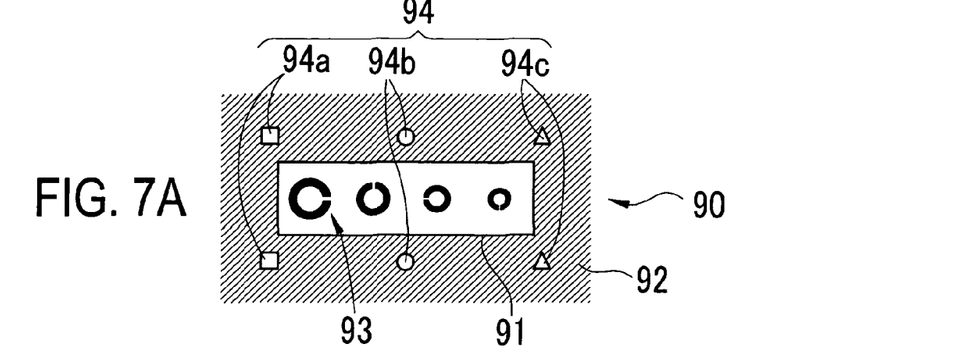
FIG. 7A is a diagram showing an optotype for a binocular balance test and how it appears.

A chart (optotype) 90 for a binocular balance test displayed and presented on the presenting part 72 includes a white (high-luminance color) rectangle 91 horizontally oriented on a black (low-luminance color) background 92 as shown in FIG. 7A. In the horizontal rectangle 91, a plurality of (four in this embodiment) letters (or symbols, etc.) 93 in black (low-luminance color) and in different sizes are arranged in a single horizontal row. On the background 92, above and below the horizontal rectangle 91, figures 94 for fusion stimulus are arranged. The figures 94 include "□"-shaped white (high-luminance color) marks 94a, "○"-shaped white (high-luminance color) marks 94b, and "Δ"-shaped white (high-luminance color) marks 94c. The marks 94a to 94c are symmetrical in pairs with respect to a horizontal straight line passing the center of the horizontal rectangle 91. The figures 94 are not limited to the above if only figures arranged in pair(s) one above the other have the same shape, size, color, etc. The number of the figures 94 has only to be at least one. For example, a pair of straight lines horizontally extending one above the other may be employed.

When the command signal for implementing the binocular balance test is inputted by operation of a predetermined button of the buttons 81, the command signal is transmitted to the arithmetic control part 73 via the arithmetic control parts 51 and 6a to display the chart 90 on the presenting part 72. Furthermore, the screen 80 appears on the display part 50. In this screen 80, a simplified diagram of the chart 90 is displayed in the section 81a, symbols representing the rotary prism 161 are displayed in the buttons 82, and a message related to the binocular balance test is displayed in the section 85.

The command signal is also transmitted to the arithmetic control part 65 via the arithmetic control parts 51 and 6a to dispose the rotary prisms 161 in the test windows 61R and 61L. At that time, the rotary prism 161 is set at 2Δ BD (Base Down) in the test window 61R and the rotary prism 161 is set at 2Δ BU (Base Up) in the test window 61L. In the screen 80, current prism powers of the rotary prisms 161 set in the test windows 61R and 61L are displayed in the section 86.

Figure 7B:
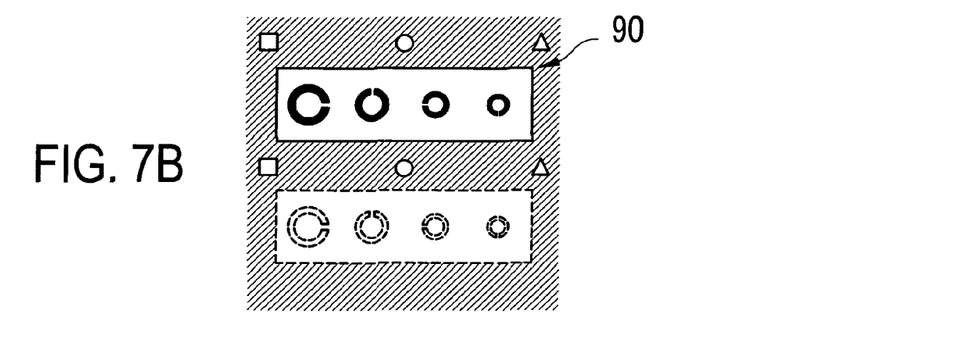
FIG. 7B is a diagram showing the optotype for a binocular balance test and how it appears.

When an examinee sees the chart 90 with the right eye, the chart 90 appears as shown in FIG. 7B. Specifically, the right eye sees the chart 90 on the presenting part 72 through the rotary prism 161 set at 2Δ BD and hence the chart 90 (the horizontal rectangle 91 and others) appears to be displaced higher than its actual position indicated by a dotted line.

Figure 7C:
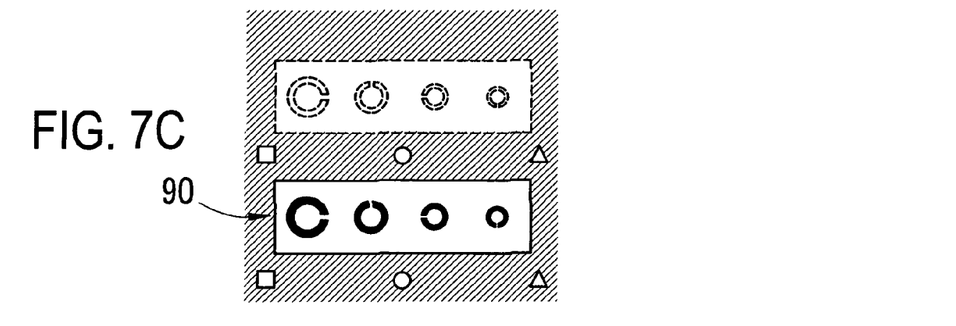
FIG. 7C is a diagram showing the optotype for a binocular balance test and how it appears.

When the examinee sees the chart 90 with the left eye, on the other hand, the chart 90 appears as shown in FIG. 7C. Specifically, the left eye sees the chart 90 on the presenting part 72 through the rotary prism 161 set at 2Δ BU and hence the chart 90 (the horizontal rectangle 91 and others) appears to be displaced lower than its actual position indicated by the dotted line.

Figure 7D:
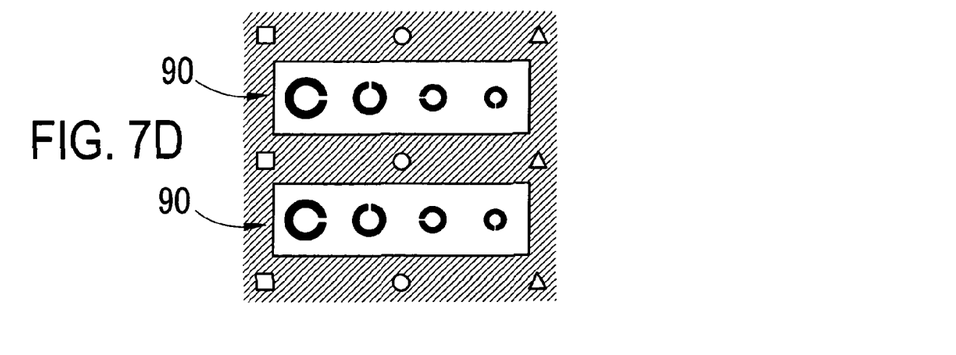
FIG. 7D is a diagram showing the optotype for a binocular balance test and how it appears.

When the examinee sees the chart 90 with both eyes, the chart 90 appears as shown in FIG. 7D. Specifically, the chart 90 appears as separated upper and lower charts. In the binocular balance test, appropriate correction powers for both eyes of the examinee are determined so that the upper and lower charts 90 appear at the same level.

The marks 94a to 94c arranged in pairs one above the other are the same in shape, size, color, and others and therefore they can be fused easily, thus facilitating comparison between the charts 90 appearing as separated upper and lower charts. With the presence of the marks 94a to 94c, the binocular balance test can be performed easily even on an examinee with heterophoria.

Furthermore, the background 92 is black (low-luminance color) and accordingly it is less likely to cause visual noise during comparison of the separately appearing upper and lower charts 90. Furthermore, the rotary prism 161 for displacing the chart 90 upward and the rotary prism 161 for displacing the chart 90 downward are equal in prism power (displacement amount). Accordingly, the chart 90 appearing to the right eye and the chart 90 appearing to the left eye are almost similar to each other except for respective positions.

The binocular balance test can be conducted as above using the prisms (the rotary prisms 161) without employing a polarization filter.

In the above explanation, the rotary prisms 161 set at 2Δ BD and 2Δ BU are used to allow the chart 90 to appear as separated upper and lower charts. However, to some examinees, the chart 90 may not appear as separated upper and lower charts or may appear as separated upper and lower charts too far apart.

In this embodiment, the prism powers of the rotary prisms 161 disposed in the test windows 61R and 61L are adjusted equally by the same prism power (the displacement amount) in response to rotation of the dial 56. As shown in the section 86 in FIG. 5, the prism power is decreased by clockwise rotation of the dial 56 and increased by counterclockwise rotation thereof. Specifically, a rotation signal of the dial 56 is transmitted to the arithmetic control part 65 via the arithmetic control parts 51 and 6a, thereby rotating the rotary prisms 161 disposed in the test windows 61R and 61L to adjust the displacement amount of the charts 90 in a vertical direction.

Furthermore, a screen 300 (see FIG. 8) for adjustment of an optotype (chart) displacement amount by means of the rotary prisms 161 may be adopted. By operation of a button 310 on the screen 300, the rotary prisms 161 disposed in the test windows 61R and 61L are rotated to decrease their prism powers by the same amount to move the separated upper and lower charts 90 closer to each other. By operation of a button 320 on the screen 300, the rotary prisms 161 disposed in the test windows 61R and 61L are rotated to increase their prism powers by the same amount to move the separated upper and lower charts 90 away from each other.

Figure 8:
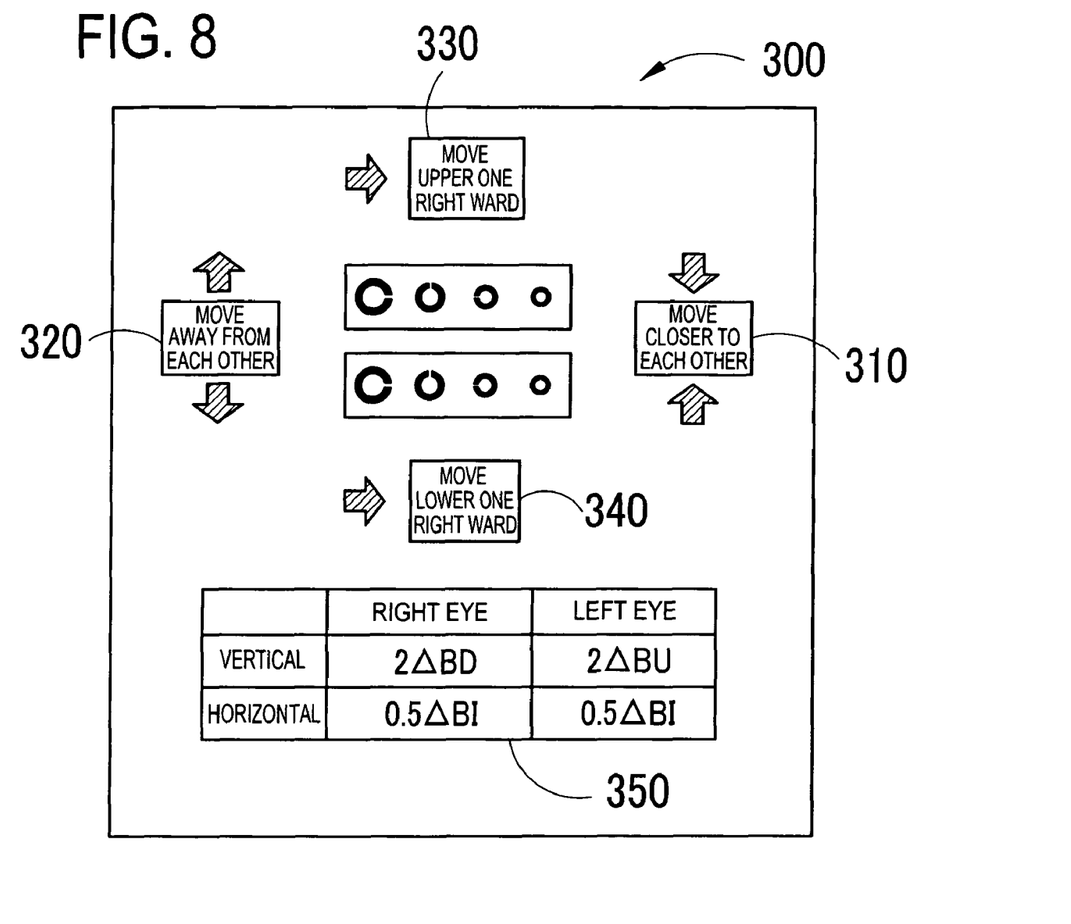
FIG. 8 is a diagram showing an example of a screen for adjustment of displacement amounts of an optotype caused by a rotary prism.

The screen 300 may also be used to adjust a horizontal displacement amount of the separately appearing upper and lower charts 90. When an upper one of the separately appearing upper and lower charts 90 is seen as being displaced leftward than a lower one, an examinee is judged to have exophoria. To the contrary, when the lower one of the separately appearing upper and lower charts 90 is seen as being displaced leftward than the upper one, an examinee is judged to have esophoria. In the case of the examinee with exophoria, accordingly, a button 330 on the screen 300 is operated to rotate the rotary prisms 161 disposed in the test windows 61R and 61L to thereby add the same BI (Base In) prism power. In the case of the examinee with esophoria, a button 340 on the screen 300 is operated to rotate the rotary prisms 161 disposed in the test windows 61R and 61L to thereby add the same BO (Base Out) prism power. The prism power in the horizontal direction is displayed in a section 350 as well as the prism power in the vertical direction.

The prism powers in the horizontal direction are changed with the rotary prisms 161 as above while the chart 90 appears as separated upper and lower charts, so that the binocular balance test can be performed even on the examinee with heterophoria. The prism powers in the horizontal direction are changed equally and thus the binocular balance test can be conducted accurately.

In the above explanation, by the rotary prisms 161, the chart 90 appears to be displaced upward to the right eye and downward to the left eye. An alternative is to cause the chart 90 to appear to be displaced downward to the right eye and upward to the left eye.

Furthermore, instead of the rotary prisms 161, a plurality of dispersion prisms having different prism powers may be mounted in the lens disk 16. For instance, when a command signal is inputted for execution of the binocular balance test, a 2Δ BD dispersion prism is disposed in the test window 61R and a 2Δ BU dispersion prism is disposed in the test window 61L.

The invention claimed is:

1. A subjective vision testing system for testing visual functions of eyes of an examinee, comprising:
   an optometric unit having right and left test windows for selectively disposing optical elements including rotary prisms in front of right and left eyes of the examinee;
   an optotype presenting unit for presenting an optotype to the examinee, the optotype presenting unit being to be disposed at a predetermined distance apart from the optometric unit and having a memory for storing image data of various optotypes and a first color display for displaying the optotype of image data read from the memory;
   a controller having various keys for inputting various command signals and a second display for displaying optometric information;
   a first control part for controlling the optotype presenting unit to present an optotype for a binocular balance test at a center of a screen of the first display based on a command signal to execute the binocular balance test from the controller, the optotype for the binocular balance test including a plurality of first letter or symbol optotypes arranged in a single horizontal row and second figure optotypes for fusion stimulus arranged in pair above and below the first optotypes and having the same shape, size, and color; and a second control part for controlling the optometric unit to dispose, based on the command signal to execute the binocular balance test, a first rotary prism in the right test window in front of the right eye of the examinee and a second rotary prism in the left test window in front of the left eye of the examinee, the second prism having a base direction vertically opposite to that of the first rotary prism and the same prism power as the first rotary prism.

2. The subjective vision testing system according to claim 1, wherein prism powers of the first rotary prism and the second rotary prism are changed equally.

* * * * *